US009833553B2

(12) United States Patent
Higgitt et al.

(10) Patent No.: US 9,833,553 B2
(45) Date of Patent: Dec. 5, 2017

(54) DIALYSIS MACHINE

(75) Inventors: Ben Higgitt, Redditch (GB); Mark Wallace, Kinver (GB); Jeremy Harrop, Broadway (GB)

(73) Assignee: Quanta Fluid Solutions Ltd., Warwickshire (GB)

( * ) Notice: Subject to any disclaimer, the term of this patent is extended or adjusted under 35 U.S.C. 154(b) by 683 days.

(21) Appl. No.: 14/379,180

(22) PCT Filed: Feb. 16, 2012

(86) PCT No.: PCT/GB2012/000162
§ 371 (c)(1),
(2), (4) Date: Dec. 1, 2014

(87) PCT Pub. No.: WO2013/110906
PCT Pub. Date: Aug. 1, 2013

(65) Prior Publication Data
US 2015/0076053 A1    Mar. 19, 2015

(30) Foreign Application Priority Data

Jan. 26, 2012 (GB) .................................. 1201330.6

(51) Int. Cl.
*A61M 1/16* (2006.01)
(52) U.S. Cl.
CPC ............ *A61M 1/1641* (2014.02); *A61M 1/16* (2013.01); *A61M 1/1601* (2014.02); *A61M 1/1635* (2014.02); *A61M 2205/126* (2013.01); *A61M 2205/128* (2013.01); *A61M 2205/3331* (2013.01); *A61M 2205/3334* (2013.01);

(Continued)

(58) Field of Classification Search
None
See application file for complete search history.

(56) References Cited

U.S. PATENT DOCUMENTS 3,605,566 A * 9/1971 Vetter .................. F04B 43/009
417/63
6,382,923 B1 * 5/2002 Gray .................. F04B 43/0081
417/53

(Continued)

FOREIGN PATENT DOCUMENTS

EP    0 623 357 A1    11/1994
EP    0623357 A1 *   11/1994 .............. A61M 1/16

OTHER PUBLICATIONS

Jan. 7, 2013 International Search Report for PCT/GB2012/000162.
Aug. 7, 2014 Transmittal of International Preliminary Report on Patentability for PCT/GB2012/000162.

*Primary Examiner* — Krishnan S Menon
*Assistant Examiner* — Bradley R Spies
(74) *Attorney, Agent, or Firm* — Hahn Loeser & Parks LLP

(57) ABSTRACT

A hemodialysis machine comprising a dialysate flow path for delivering a flow of dialysate solution through a dialyser, the flow path including a flow balancer for achieving a balance in the dialysate solution flow volume observed between an inlet and an outlet of the dialyser over the course of a treatment, the flow balancer comprising a first flow balance pump having an inlet valve and an outlet valve and a second flow balance pump having an inlet valve and an outlet valve, wherein the flow path further includes a flow restrictor means downstream of the flow balance pumps to reduce the pressure difference across the valves in the dialysate flow path.

14 Claims, 8 Drawing Sheets

(52) U.S. Cl.
CPC .............. *A61M 2205/3344* (2013.01); *A61M 2205/3379* (2013.01)

(56) References Cited

U.S. PATENT DOCUMENTS

| | | | |
|---|---|---|---|
| 2009/0012460 A1* | 1/2009 | Steck | A61M 1/28 604/30 |
| 2010/0089807 A1* | 4/2010 | Heyes | A61M 1/16 210/96.2 |
| 2010/0192686 A1 | 8/2010 | Kamen et al. | |
| 2010/0290935 A1* | 11/2010 | Richter | F04B 43/043 417/413.2 |
| 2011/0015610 A1* | 1/2011 | Plahey | A61M 1/28 604/500 |
| 2011/0303588 A1 | 12/2011 | Kelly et al. | |
| 2011/0315611 A1 | 12/2011 | Fulkerson et al. | |

* cited by examiner

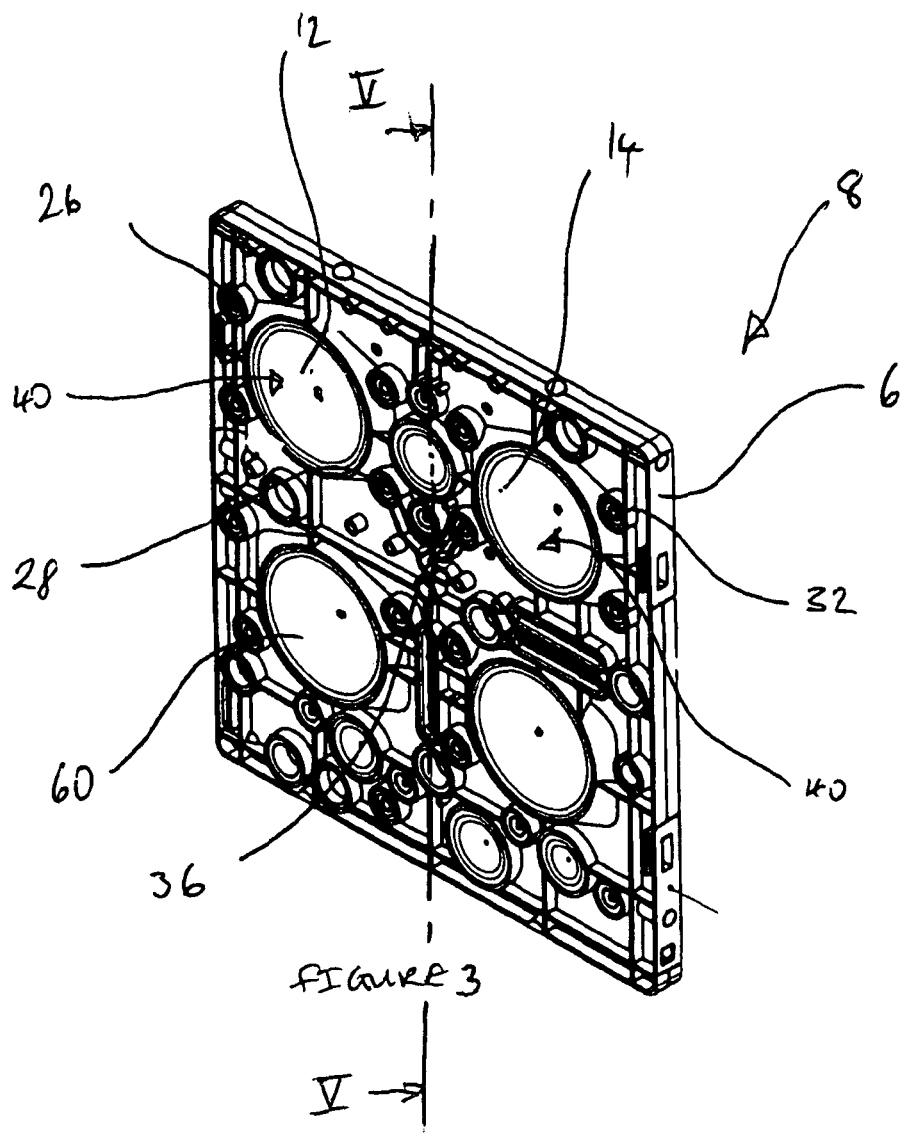

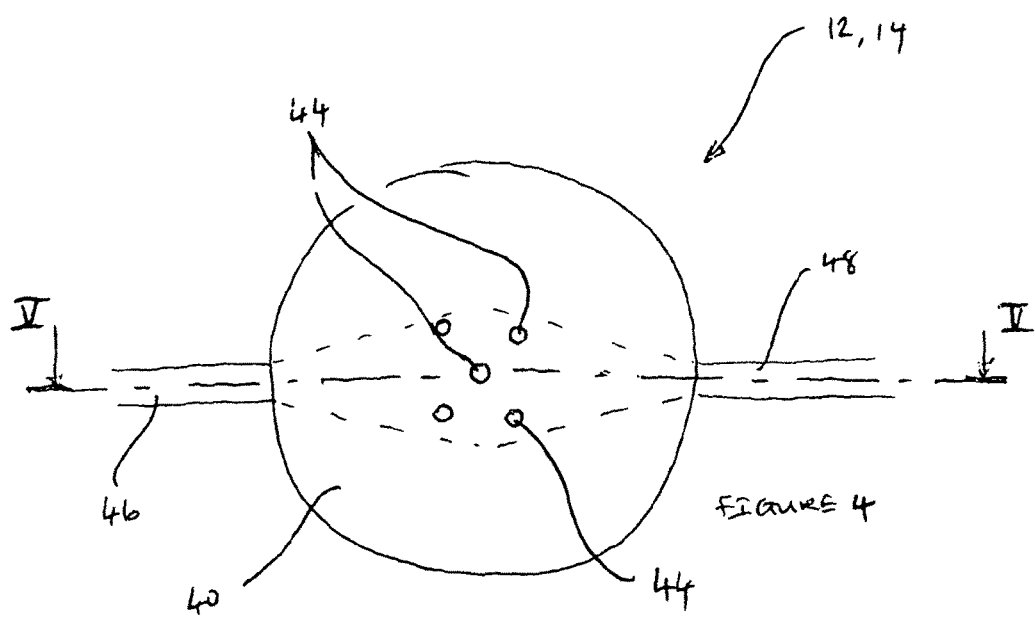
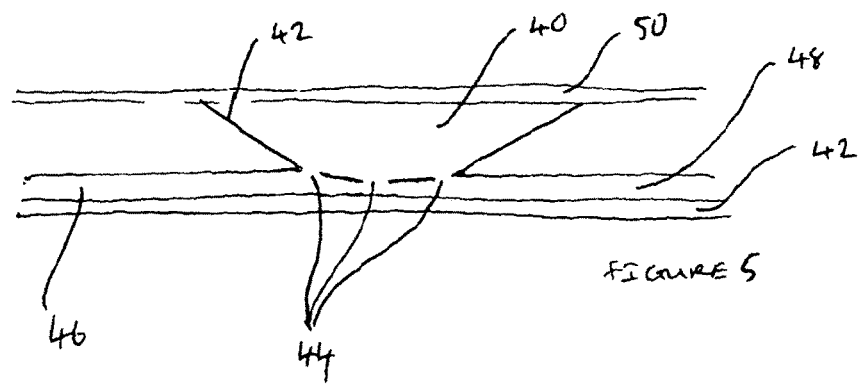

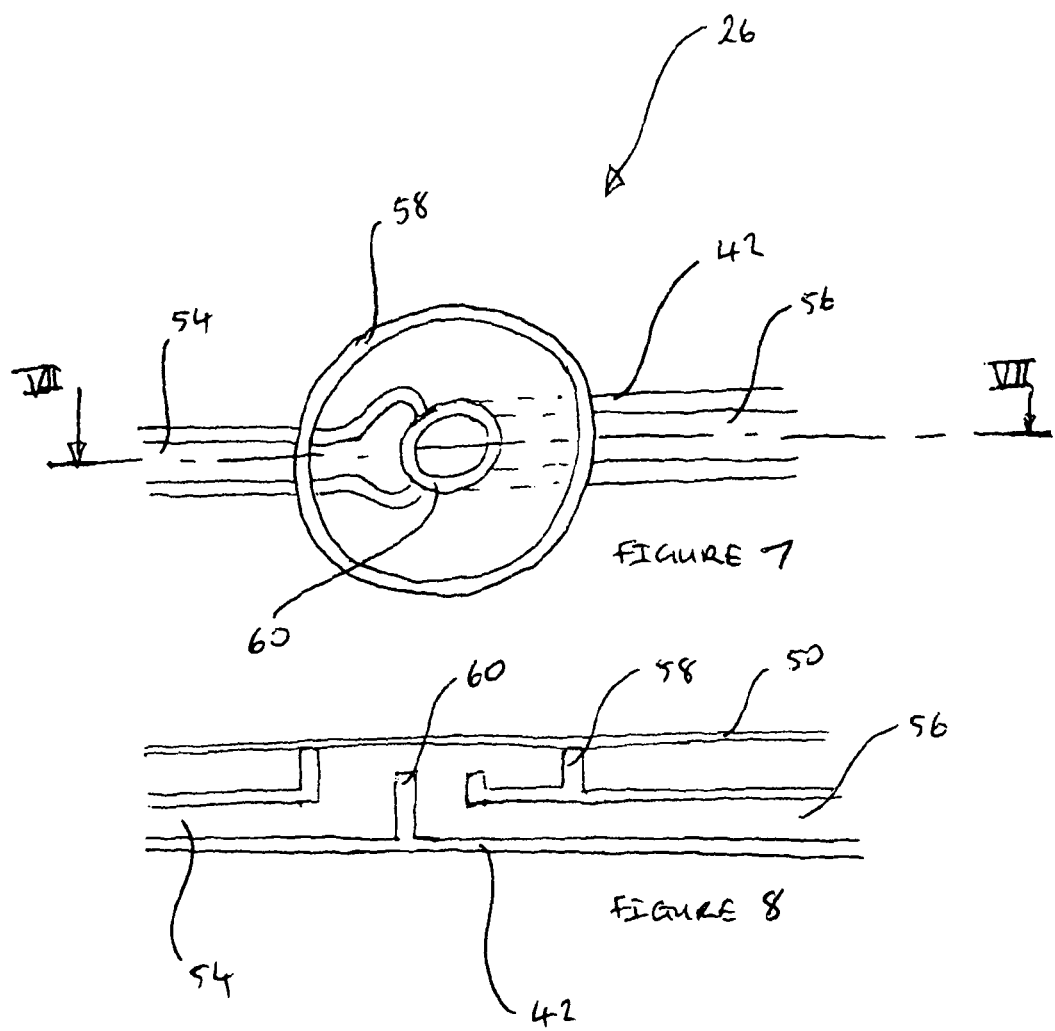

DIALYSIS MACHINE

The present application is a §371 submission of international application no. PCT/GB2012/000162, which was filed on 16 Feb. 2012 and entitled Dialysis Machine, which was published in the English language on 1 Aug. 2013 with publication no. WO 2013/110906 A1, and which claimed the benefit of the filing date of GB 1201330.6, filed 26 Jan. 2012.

The present invention relates to dialysis machines and in particular, but not exclusively, to a disposable cartridge for use in hemodialysis machine.

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis.

In peritoneal dialysis treatment, a dialysate solution is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to hemodialysis at a later stage.

In hemodialysis, the patient's blood is removed from the body by an arterial line, is treated by the dialysis machine, and is then returned to the body by a venous line. The machine passes the blood through a dialyser containing tubes formed from a semi permeable membrane. On the exterior of the semi permeable membrane is a dialysate solution. The semi permeable membrane filters the waste products and excess fluid from the blood into the dialysate solution. The membrane allows the waste and a controlled volume of fluid to permeate into the dialysate whilst preventing the loss of larger more desirable molecules, like blood cells and certain proteins and polypeptides.

The action of dialysis across the membrane is achieved primarily by a combination of diffusion (the migration of molecules by random motion from a region of higher concentration to a region of lower concentration), and convection (solute movement that results from bulk movement of solvent, usually in response to differences in hydrostatic pressure).

Fluid removal (otherwise known as ultrafiltration) is achieved by altering the hydrostatic pressure of the dialysate side of the membrane, causing free water to move across the membrane along the pressure gradient.

The correction of uremic acidosis of the blood is achieved by use of a bicarbonate buffer. The bicarbonate buffer also allows the correction of the blood bicarbonate level.

The dialysis solution consists of a sterilized solution of mineral ions. These ions are contained within an acid buffer which is mixed with the serilised water and bicarbonate base prior to delivery to the dialyser.

Dialysate composition is critical to successful dialysis treatment since the level of dialytic exchange across the membrane, and thus the possibility to restore adequate body electrolytic concentrations and acid-base equilibrium, depends on the composition.

The correct composition is accomplished primarily by formulating a dialysate whose constituent concentrations are set to approximate normal values in the body.

However, achieving the correct composition of dialysate requires the accurate control of low volumes of liquid and at present this is achieved by the provision of complex fluid paths, including multiple pumping and valving components on the dialysis machine.

Furthermore the balance of fluids across the dialyser is critical in providing effective treatment. Any instability in the fluid pressure control can therefore have a detrimental effect on the quality of the treatment.

Such instability can be introduced into a fluidic system by, for example, the fluidic displacement caused by valve actuation, pressure variations caused by complex flow paths and unintended flow restrictions.

It is an object of the present invention to provide a hemodialysis system which at least mitigates some of the problems described above.

According to a first aspect of the invention there is provided a hemodialysis machine comprising:

a dialysate flow path for delivering a flow of dialysate solution through a dialyser, the flow path including:
  a flow balancer for achieving a balance in the dialysate solution flow volume observed between an inlet and an outlet of the dialyser over the course of a treatment, the flow balancer comprising a first flow balance pump having an inlet valve and an outlet valve and a second flow balance pump having an inlet valve and an outlet valve,
wherein the flow path further includes a flow restrictor means downstream of the flow balance pumps to reduce the pressure difference across the valves in the dialysate flow path.

Since the arterial and/or venous blood line pressures vary during the course of a treatment, for example by variation in patient blood pressure or by patient venous and arterial access elevation, it follows that the pressures in the dialysate line at the inlet and outlet to the dialyser also vary by way of pressure transfer across the dialyser from the blood line to the dialysate line. This causes inaccuracies in flow balance over the course of a treatment in prior art devices.

Advantageously, in the present invention, the use of a flow restrictor downstream of the pumps reduces the pressure difference across the valves (and any other compliant structures in the flow path) at the time of closure of the valve by introducing a back-pressure into the dialysate line. This reduction in pressure difference reduces the variance in the position of the compliant structures, predominantly the valves, in the fluid line. This in turn ensures the volumetric balance of the dialysate fluid entering and leaving the dialyser thereby improving flow balance accuracy.

Preferably, the machine includes a disposable cartridge, the cartridge defining the dialysate flow path.

Preferably, the pumps are switchable between two modes of operation, a first mode of operation in which the first flow balance pump is arranged in the dialysate line upstream of said dialyser and the second flow balance pump is arranged in the dialysate line downstream of said dialyser, and a second mode of operation in which the second flow balance pump is arranged in the dialysate line upstream of said dialyser and the first flow balance pump is arranged in the dialysate line downstream of said dialyser.

Preferably, the flow restrictor forms part of the flow path on the cartridge.

According to a second aspect of the invention there is provided a hemodialysis machine comprising:

a dialysate flow path for delivering a flow of dialysate solution through a dialyser, the flow path including:

a flow balancer for achieving a balance in the dialysate solution flow volume observed between an inlet and an outlet of the dialyser over the course of a treatment, the flow balancer comprising a first flow balance pump having an inlet valve and an outlet valve and a second flow balance pump having an inlet valve and an outlet valve, wherein each of the valves has a pneumatically operable membrane covering an inlet port and an outlet port, the valves being substantially geometrically identical to oneanother.

Advantageously, by providing valves that are substantially geometrically identical, the present invention ensures that the closure position of all of the valves for a given pressure difference will be uniform. Thus the volume of fluid displaced by the valves upon actuation will be uniform leading to improved accuracy of flow balance.

Preferably, the pumps are switchable between two modes of operation, a first mode of operation in which the first flow balance pump is arranged in the dialysate line upstream of said dialyser and the second flow balance pump is arranged in the dialysate line downstream of said dialyser, and a second mode of operation in which the second flow balance pump is arranged in the dialysate line upstream of said dialyser and the first flow balance pump is arranged in the dialysate line downstream of said dialyser.

Preferably, the inlet port is arranged coaxially within the outlet port such that the cross-sectional area of the inlet port is less that the outlet port.

Preferably, the machine includes a disposable cartridge, the cartridge defining the dialysate flow path.

According to a third aspect of the invention there is provided a hemodialysis machine comprising:

a dialysate flow path for delivering a flow of dialysate solution through a dialyser wherein the flow path includes:

a pump for pumping dialysate solution, the pump having a pump chamber defining a fluid access port, the fluid access port being in fluid communication with an inlet valve and an outlet valve, p1 wherein the fluid access port is defined by two or more apertures in the pump chamber.

The provision of a fluid access port having multiple apertures has at least two advantages. Firstly, the membrane does not descend into the apertures at the end of the pump stroke as it does when one large aperture (having the same cross-sectional area as the combined 5 smaller apertures) is provided. This increases the life of the membrane and improves the accuracy of the pump stroke volume. Secondly the, pressure in the fluid line downstream of the pump at the end of the stroke is reduced. As the membrane is actuated into the pump chamber the outermost holes are covered first leading to a reduced cross-sectional area of fluid outlet at the end of the stroke. This acts to damp the downstream pressure preventing the establishment of a pressure wave in the downstream fluid which can lead to volumetric errors in the downstream pumps and valves.

Preferably, the fluid access port is a combined inlet/outlet to the pump chamber.

Preferably, the fluid access port is defined by five apertures in the pump chamber.

Preferably, the access port is defined by one central aperture surrounded by four apertures concentric with the central aperture.

Preferably, the machine includes a disposable cartridge, the cartridge defining the dialysate flow path.

The invention will now be described, by way of example only, and with reference to the following drawings, in which:

FIG. 3 is an isometric view of a dialysis cartridge of the machine of FIG. 2;

FIG. 4 is a plan view of a portion of the cartridge of FIG. 3, showing the pump chamber in greater detail;

FIG. 5 is a sectioned side view along line V-V of the pump chamber of FIG. 4;

FIG. 7 is a plan view of a portion of the cartridge of FIG. 3, showing the valve in greater detail;

FIG. 8 is a sectioned side view along line VII-VII of the valve of FIG. 7, with the valve in its open position;

Figure 1:
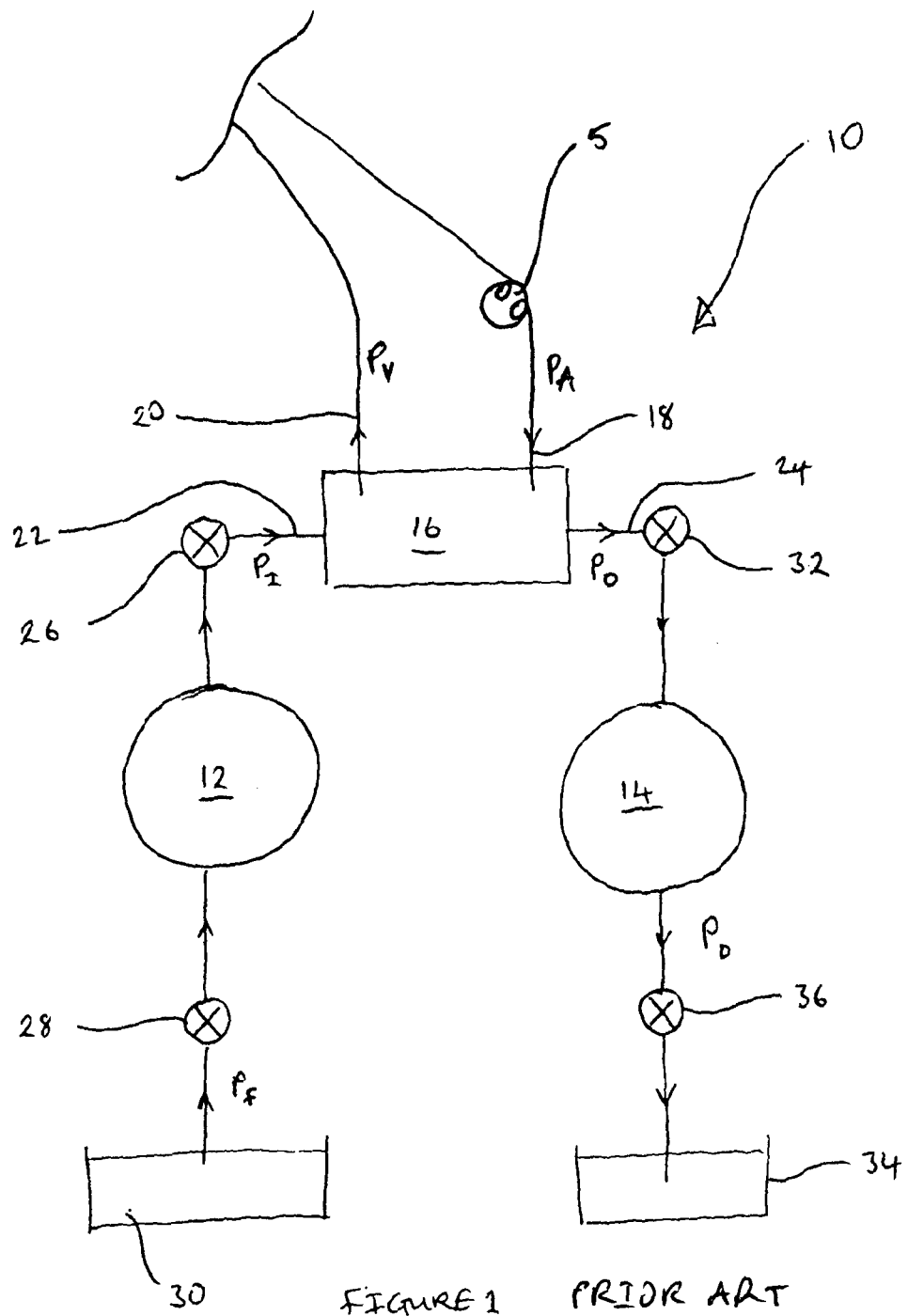
FIG. 1 is a schematic view of a prior art dialysis system.

Referring to FIG. 1, a dialysis system 10 is shown having a dialysate distribution pump in the form of a flow balance pump having a first flow balance chamber 12 and a second flow balance chamber 14. A dialyser 16 receives blood via an arterial line 18 connected to the patient by a vascular access device (not shown for clarity). The blood is pumped from the patient to the dialyser by a pump 5, typically a peristaltic pump. The blood passes through the dialyser in a known manner and is returned to the patient via a venous line 20. The dialyser 16 also has a dialysate inlet line 22 for receiving fresh dialysate and a dialysate outlet line 24 for removing the spent dialysate from the dialyser 16. In this way the waste products in the blood pass into the dialysate across a semipermiable membrane in a known manner.

Upstream of the dialysate inlet line 22 is a dialyser inlet valve 26 which controls the passage of dialysate into the dialyser 16. Dialysate is pumped into the dialyser 16 via the dialyser inlet valve 26 by the first flow balance pump 12. Upstream of the first flow balance pump chamber 12 is a flow balance pump inlet valve 28. The first flow balance pump chamber 12 is configured to draw dialysate from a dialysate source 30 via the flow balance pump inlet valve 28.

On the dialysate outlet side of the dialyser 16 is a dialysate outlet valve 32 which controls the flow of spent dialysate in the dialysate outlet line 24. The second flow balance pump chamber 14 draws spent dialysate through the dialysate outlet valve 32 and to a drain 34 via a flow balance pump outlet valve 36.

In use the flow balance pump inlet valve 28 is opened and the first flow balance pump chamber 12 is actuated to draw dialysate fluid from the dialysate source 30 into the first flow balance pump chamber 12. The flow balance pump inlet valve 28 is then closed, the dialyser inlet valve 26 opened and the first flow balance pump chamber 12 is actuated to pump dialysate into the dialyser 16.

At the same time as the first flow balance pump 12 chamber, flow balance pump inlet valve 28 and dialyser inlet valve 26 are being operated upstream of the dialyser to pump dialysate into the dialyser 16, the second flow balance pump chamber 14, dialysate outlet valve 32 and flow balance pump outlet valve 36 are operated as follows to draw dialysate form the dialyser 16.

The dialysate outlet valve 32 is opened and the second flow balance pump chamber 14 is actuated in order to draw dialysate from the dialyser 16 into the second flow balance pump chamber 14. The dialysate outlet valve 32 is then closed, the flow balance pump outlet valve 36 opened and the second flow balance pump chamber 14 is actuated to pump dialysate from the second flow balance pump chamber 14 to the drain 34.

This cycle of pumping is then repeated in order to draw a constant flow of dialysate from the dialysate source 30, through the dialyser 16 and to the drain 34.

Figure 2:
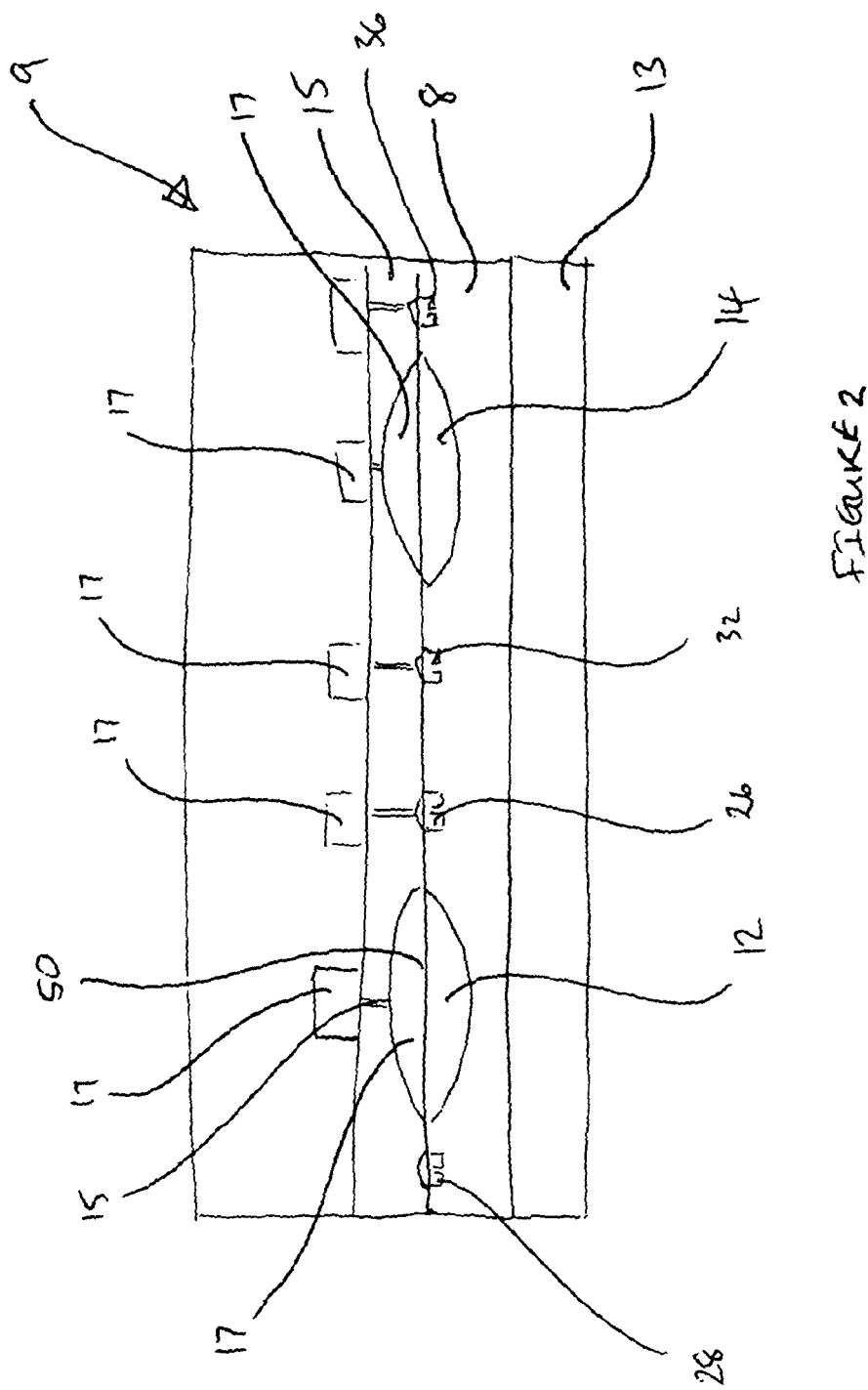
FIG. 2 is a sectioned side view of a dialysis machine of the present invention.

The dialysis system described above is embodied by a dialysis machine shown schematically at 9 in FIG. 2. The machine 9 includes the features of the prior art system described above and features of the present invention that will be described shortly. The machine operates a cartridge 8 (see FIG. 3) which in part embodies the pump chambers 12, 14 and valves 26, 28, 32, 36 as will be seen in further detail shortly. The cartridge 8 has a rigid body 6 covered by a flexible film 50 (shown in FIG. 2 only). The pump chambers 12, 14 are in part defined by concave pump cavities 40 formed by the body 6 of the cartridge.

The operation of the first and second flow balance pump chambers can be switched to allow the second pump chamber 14 to pump fluid into the dialyser and the first balance pump 12 to pump fluid out of the dialyser. This balances over the course of the treatment any geometric differences between the chambers resulting from the cartridge manufacturing process. Furthermore, by mirroring the valves 26, 28, 32, 36 and pump chambers 12, 14 about centreline A-A in FIG. 3 any fluidic variation is eliminated as the fluid path is fluidically substantially identical irrespective of which pump chamber 12, 14 is pumping into or out of the dialyser.

In use the cartridge 8 is retained between a first platen 13 on one side of the cartridge and a second platen 15 on a second side of the cartridge. The second platen 15 defines cavities 17 which match the concave pump cavities 40 on the cartridge. The pumps are operated by pneumatically actuating the film 50 in order to draw fluid into and out of the pump chambers. This is achieved by pneumatic actuators 17 applying pressure and vacuum to the film 50 via channels 15 in a known manner. Similarly the valves 26, 28, 30, 32 are operated by pneumatic actuators 17. A controller (not shown for clarity) controls the actuators 17 to open and close the valves and operate the pumps as will be described in further detail shortly.

Referring now to FIGS. 4 and 5, the first and second flow balance pump chambers 12, 14 are shown in more detail. The pump cavity 40 has a lower wall 42 which defines a series of apertures 44 which allows access to the pump cavity 40 via the pump inlet 46 and pump outlet 48. The apertures are arranged with one central aperture surrounded by four concentric outer apertures.

In the first flow balance pump chamber 12 the pump inlet 46 is fluidically connected to the flow balance pump inlet valve 28 and the pump outlet 48 to the dialyser inlet valve 26. In the second flow balance pump chamber 14 the pump inlet 46 is fluidically connected to the dialysate outlet valve 32 and the pump outlet 48 to the flow balance pump outlet valve 36.

The pump cavity 40 is enclosed by the flexible film 50 which is actuated by the actuator 17 applying pressure, or vacuum, to the outer surface of the film 50. When the actuator applies a vacuum to the film, the film moves into the cavity 17 in the platen 15 (see FIG. 2) thereby drawing dialysate into the pump chamber. This is referred to as the inlet stroke of the pump. The inlet valve 28, 32 is then closed, the outlet valve 26, 36 opened and pressure applied to the film 50 in order to pump the dialysate out of the pump cavity and through the outlet valve (the outlet stroke of the pump). Once the pump has expelled the dialysate (or a predetermined proportion thereof) from the pump cavity 40, the actuator stops applying the pnemautic pressure to the film and the outlet valve is closed a predetermined fixed period of time after completion of the outlet stroke. This process is then repeated by reciprocating the film under pressure and vacuum to pump dialysate through the pump.

Figure 6A:
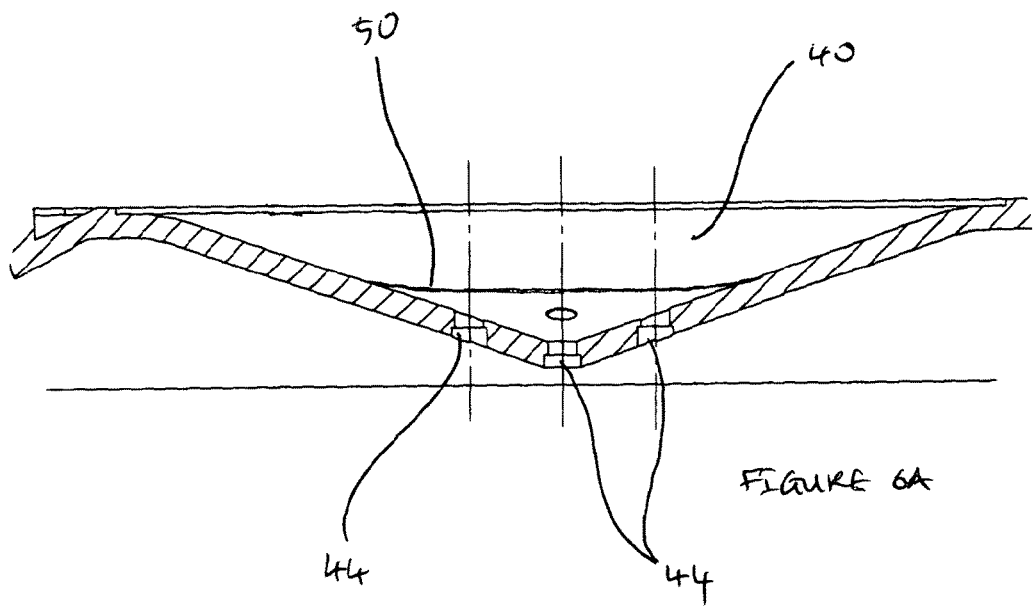
FIG. 6A is a detailed view of a portion of the sectioned view of FIG. 5 showing the membrane in a first position.

In FIG. 6A the membrane is shown in a first position in which the pump chamber has been partly evacuated under the action of the membrane. In this position all five of the apertures 44 are exposed, that is to say that fluid is able to exit through all five apertures under the action of the membrane.

Figure 6B:
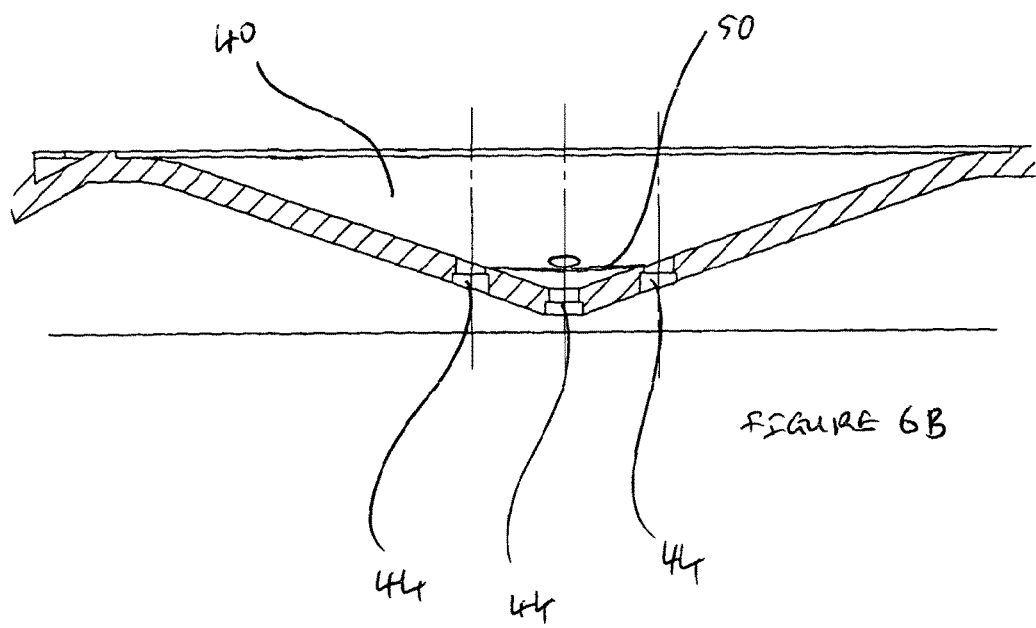
FIG. 6B is a detailed view of a portion of the sectioned view of FIG. 5 showing the membrane in a second position.

In FIG. 6B the membrane is shown in a second position. The membrane has descended further into the pump chamber than in FIG. 6B as it approaches the end of its pump stroke. In this position, the four outer apertures are covered by the membrane, leaving only the central aperture available to permit fluid to exit the chamber.

As a result the flow rate out of the chamber at the end of the stroke is reduced as the cross-sectional area of aperture available to the fluid has reduced by 80%. This reduces the pressure downstream of the pump chamber at the end of the stroke which reduces the magnitude of the pressure wave induced in the downstream fluid when the membrane gets to the end of its travel. This reduces the fluid hammer effect of operating the pumps and also aids the normalisation of the pressure differential across the valve membrane downstream of the pump.

Referring now to FIGS. 7 and 8, the dialyser inlet valve 26 is shown in greater detail but the description applies equally to all of the valves 26, 28, 32, 36 which are essentially identical. The valve 26 is defined by the rigid body 9 of the cartridge 8 shown in FIG. 2. Each valve has an inlet 54 and an outlet 56. The valve has an outer upstanding wall 58 and an inner upstanding wall 60. The inner upstanding wall 60 stands slightly lower than the outer upstanding wall 58. The valve is covered by the same flexible film 50 as the pumps 12, 14 and the film 50 is pneumatically actuable by actuators 17 in a similar manner to open and close the valves as will be described in further detail below. In FIG. 7 the valve is shown in its open position in which dialysate can enter the valve via the inlet 54, pass over the inner upstanding wall 60 and out of the outlet 56. Thus, the flow of fluid is up through an outer inlet, over the valve seat 60 and out through an inner inlet. This means that all of the valves have substantially the same crack pressure and will all deform the membrane upon closing in a substantially uniform way. This uniformity through the system assists in mitigating the variation in closure position of the valves which leads to an improved accuracy of flow balance. It is conceivable within the scope of the invention that the inlet and outlet on all the valves are switched, that is to say that the flow of fluid is up through a central inlet, over the valve seat 60 and down an outer outlet.

Figure 9A:
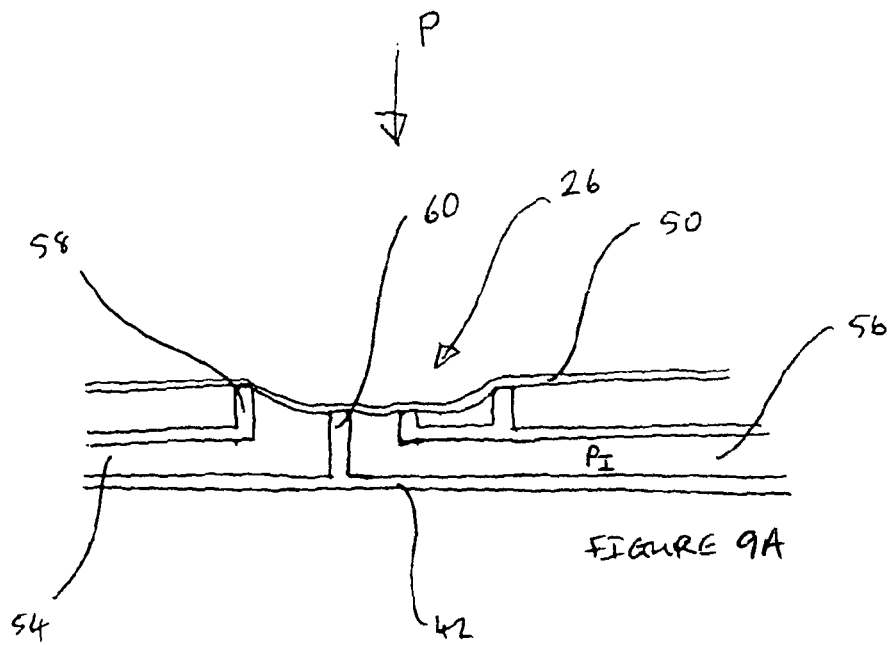
FIG. 9A is a sectioned side view along line VII-VII of the valve of FIG. 7, with the valve in its first closed position.

Turning now to FIG. 9A, the valve is shown in a first closed position in which the film 50 has been actuated by the application of pressure by actuator 17 to the outer surface of the film in a known manner. This application of pressure P has caused the film 50 to deflect causing the film contact the inner upstanding wall 60 thus creating a barrier between the inlet 54 and outlet 56.

Referring briefly to FIG. 1, The outlet 56 of the dialyser inlet valve 26 is subject to a pressure $P_1$. As the patient blood pressure varies during the treatment the arterial line inlet pressure $P_A$ and the venous line pressure $P_V$ vary accordingly. This variation in pressure is passed across the semipermeable membrane in the dialyser 12 to cause the pressure $P_1$ in the outlet 56 of the dialyser inlet valve 26 to vary.

Figure 9B:
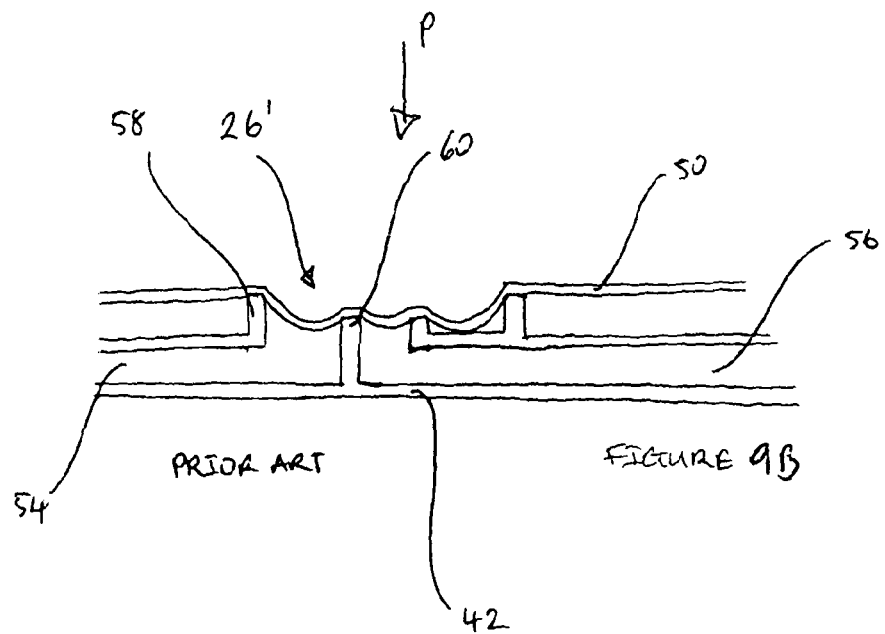
FIG. 9B is a sectioned side view along line VII-VII of the valve of FIG. 7, with the valve in its second closed position.

Turning now to FIG. 9B, the effects of this variation on the valve 26 is shown. The valve 26 is the same as the valve 26 shown in FIG. 8. The difference is that the film 50 has deflected further than the position shown in FIG. 8 despite the same pressure P being applied to the outer surface of the film 50.

This variation in the deflection position of the film 50 upon actuation of the film 50 results in the swept volume of the valve 26, that is to say the volume of dialysate displaced downstream by the actuation of the valve 26, varying in an unpredictable manner throughout the treatment in prior art devices. This same effect is experienced by the flow balance pump inlet valve 28 and the dialysate outlet valve 32 with the effect that the accumulation of variation of displaced volume can lead to significant flow balance errors over the duration of the treatment in prior art devices.

Figure 10:
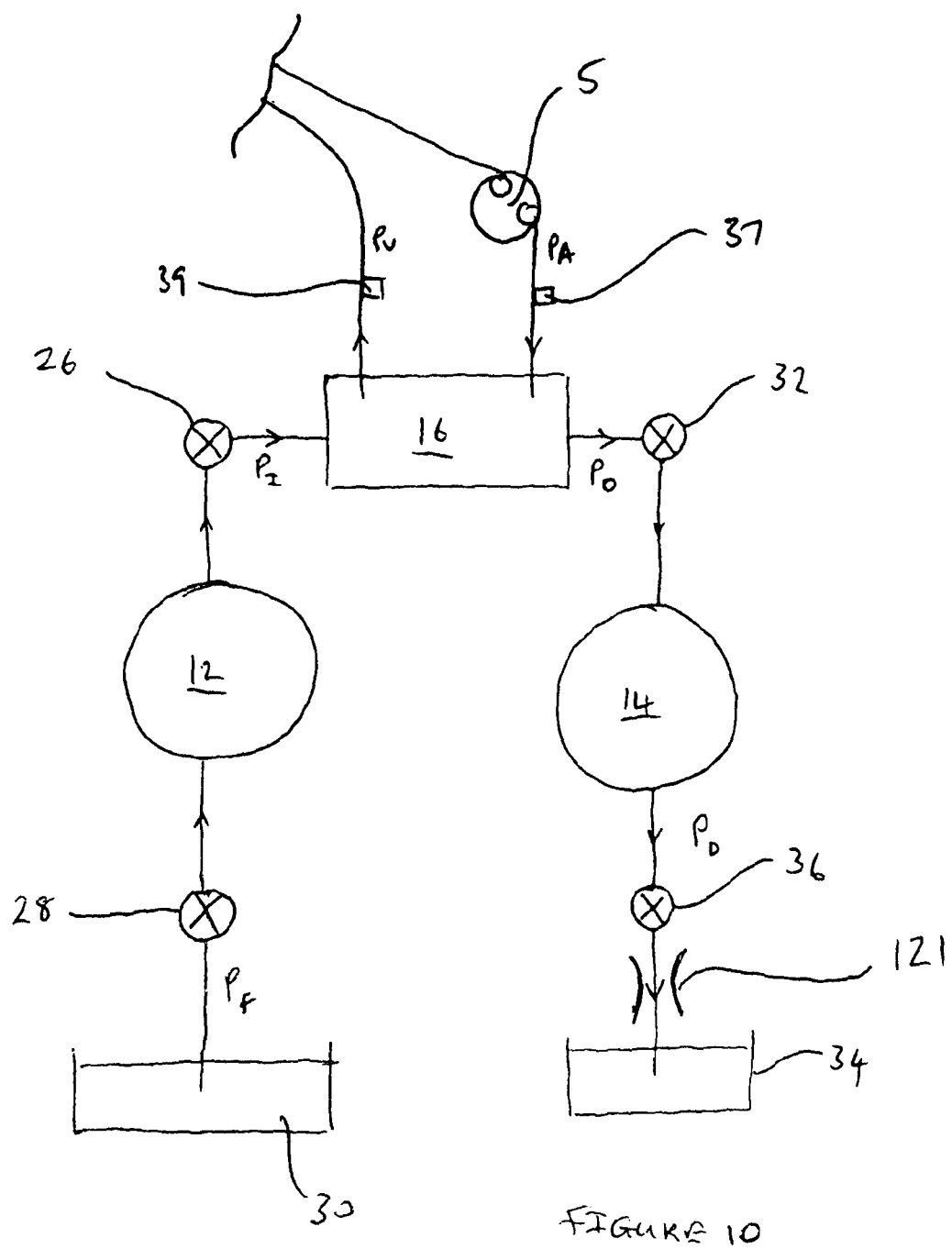
FIG. 10 is a schematic view of a dialysis system according to the present invention.

With reference to FIG. 10, the present invention overcomes this error by the use of a flow restriction 121 in the drain line. The use of a flow restrictor downstream of pumps reduces the pressure difference across the valves (and any other compliant structures in the flow path) at the time of closure of the valve by introducing a back-pressure into the dialysate line. This reduction in pressure difference reduces the variance in the position of the compliant structures, predominantly the valves, in the fluid line. This in turn ensures the volumetric balance of the dialysate fluid entering and leaving the dialyser thereby improving flow balance accuracy.

The restriction is embodied by a constriction in the form of a section of reduced diameter tubing between the cartridge and the drain. The flow restriction could alternatively be defined on the cartridge without departing from the scope of the invention.

The invention claimed is:

1. A hemodialysis machine comprising:
a dialysate flow path for delivering a flow of dialysate solution through a dialyser, the flow path including:
a flow balancer for achieving a balance in the dialysate solution flow volume observed between an inlet and an outlet of the dialyser over the course of a treatment, the flow balancer comprising a first flow balance pump having an inlet valve and an outlet valve and a second flow balance pump having an inlet valve and an outlet valve, wherein each of the inlet valves and outlet valves is opened and closed by a flexible film which is pneumatically actuated such that the inlet valve and the outlet valves are compliant structures;
wherein the dialysate flow path further includes a flow restrictor downstream of the flow balance pumps to reduce the pressure difference across the valves in the dialysate flow path and, consequently, a variance in positions of those compliant structures, the flow restrictor being a section of the flow path having reduced diameter tubing; and
wherein the machine includes a disposable cartridge, the cartridge defining the dialysate flow path.

2. The machine according to claim 1 wherein the pumps are switchable between two modes of operation, a first mode of operation in which the first flow balance pump is arranged in the dialysate line upstream of said dialyser and the second flow balance pump is arranged in the dialysate line downstream of said dialyser, and a second mode of operation in which the second flow balance pump is arranged in the dialysate line upstream of said dialyser and the first flow balance pump is arranged in the dialysate line downstream of said dialyser.

3. A hemodialysis machine comprising:
a dialysate flow path for delivering a flow of dialysate solution through a dialyser, the flow path including:
a flow balancer for achieving a balance in the dialysate solution flow volume observed between an inlet and an outlet of the dialyser over the course of a treatment, the flow balancer comprising a first flow balance pump having an inlet valve and an outlet valve and a second flow balance pump having an inlet valve and an outlet valve;
wherein each of the valves is covered by a pneumatically operable membrane for operating the valve, the valves being substantially geometrically identical to one another;
wherein a physical positioning of the first and second flow balance pumps and the inlet and outlet valves is mirrored about a centreline;
wherein the dialysate flow path includes a flow restrictor downstream of the flow balance pumps, and the flow restrictor is a section of the flow path having a reduced diameter; and
wherein the pumps are switchable between two modes of operation, a first mode of operation in which the first flow balance pump is arranged in the dialysate line upstream of said dialyser and the second flow balance pump is arranged in the dialysate line downstream of said dialyser, and a second mode of operation in which the second flow balance pump is arranged in the dialysate line upstream of said dialyser and the first flow balance pump is arranged in the dialysate line downstream of said dialyser.

4. The machine according to claim 3 wherein each of the valves has an inner upstanding wall within an outer upstanding wall and which stands lower than the outer upstanding wall.

5. The machine according to claim 3 wherein the machine includes a disposable cartridge, the cartridge defining the dialysate flow path.

6. A hemodialysis machine comprising:
a dialysate flow path for delivering a flow of dialysate solution through a dialyser wherein the flow path includes:
a pump for pumping dialysate solution, the pump having a pump chamber defining a fluid access port, the fluid access port being in fluid communication with an inlet valve and an outlet valve;
wherein the fluid access port is a combined inlet/outlet to the pump chamber;
wherein the fluid access port is defined by one central aperture surrounded by four outer apertures, concentric with the central aperture, through which the dialysate solution enters or exits the pump chamber;
wherein the pump chamber is configured such that, during a portion of an outlet stroke of the pump, the four outer apertures are covered leaving only the central aperture able to permit fluid to exit the pump chamber so as to reduce pressure downstream at an end of the outlet stroke; and
wherein the machine includes a disposable cartridge, the cartridge defining the dialysate flow path.

7. The machine according to claim 1, wherein a physical positioning of the first and second flow balance pumps and the inlet and outlet valves is mirrored about a centreline of the cartridge.

8. The machine according to claim 1, wherein the disposable cartridge comprises a rigid body covered by the flexible film so as to define the dialysate flow path.

9. The machine according to claim 8, wherein the first and second flow balance pumps are actuated by pneumatically actuating the flexible film.

10. The machine according to claim 5, where in the disposable cartridge comprises a rigid body covered by a flexible film so as to define the flow path, the flexible film comprising the pneumatically operable membrane.

11. The machine according to claim 10, wherein the first and second flow balance pumps are actuated by pneumatically actuating the flexible film.

12. The machine according to claim 6, wherein the disposable cartridge comprises a rigid body covered by a flexible film so as to define the flow path.

13. The machine according to claim 12, wherein the pump is actuated by pneumatically actuating the flexible film.

14. The machine according to claim 6, wherein the dialysate flow path includes a flow restrictor downstream of the pump and of the dialyser, and the flow restrictor is a section of the flow path having a reduced diameter.

\* \* \* \* \*

UNITED STATES PATENT AND TRADEMARK OFFICE
CERTIFICATE OF CORRECTION

PATENT NO. : 9,833,553 B2
APPLICATION NO. : 14/379180
DATED : December 5, 2017
INVENTOR(S) : Higgitt et al.

Page 1 of 1

It is certified that error appears in the above-identified patent and that said Letters Patent is hereby corrected as shown below:

In the Specification

In Column 3, Line 41, delete "outlet valve, p1" and substitute therefor --outlet valve--.

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*